United States Patent [19]

Yankee et al.

[11] Patent Number: 4,581,462

[45] Date of Patent: Apr. 8, 1986

[54] PYRROLIZIDINE-3-ONES

[75] Inventors: Ernest W. Yankee, Kalamazoo, Mich.; Ronald H. Rynbrandt, deceased, late of Portage, Mich., by LeAnna C. Rynbrandt, personal representative

[73] Assignee: The Upjohn Company, Kalamazoo, Mich.

[21] Appl. No.: 526,320

[22] Filed: Aug. 25, 1983

[51] Int. Cl.$^4$ .......................................... C07D 487/06
[52] U.S. Cl. ................................... 548/453; 546/121; 548/517; 549/451; 560/156
[58] Field of Search ...................... 546/121; 548/453

[56] References Cited

FOREIGN PATENT DOCUMENTS 95345  5/1982  European Pat. Off. ............ 548/453

OTHER PUBLICATIONS

Sumoto, et al., J. Heterocyclic Chem. 18:413 (1981).
Cheng, et al., J. Amer. Chem. Soc. 103:2090 (1981).
LaLonde, et al., J. Org. Chem. 45:3664–3671 (1980).
Buchs, et al., J. Org. Chem. 47:719 (1982).

Primary Examiner—Glennon H. Hollrah
Assistant Examiner—D. B. Springer
Attorney, Agent, or Firm—Lawrence T. Welch

[57] ABSTRACT

The present invention provides certain 2,3-didehydro-5-oxopyrrolizidinones and indolizidinones which are useful as lipid-altering and anti-atherosclerotic agents.

13 Claims, No Drawings

PYRROLIZIDINE-3-ONESDESCRIPTION

BACKGROUND OF THE INVENTION

The present specification provides novel compositions of matter, novel methods of their preparation, and novel intermediates therefor. In particular, the present invention relates to 2,3-didehydro-5-oxopyrrolizidinones and indolizidinones which are useful as lipidaltering and anti-atherosclerotic agents.

Atherosclerosis in mammals is a disease characterized by the deposition of atherosclerotic plaque on arterial walls. While atherosclerosis exhibits many varied forms and consequences, typical consequences of atherosclerotic diseases include angina pectoris, myocardial infarction, stroke, and transient cerebral ischemic attacks. Other forms of atherosclerotic diseases include certain peripheral vascular diseases and other ischemias (e.g., bowel and renal).

Medical science now recognizes that certain forms of atherosclerosis may be preventable or reversible. Agents capable of preventing or reversing atherosclerosis are characterized as exhibiting antiatherosclerotic activity. Since serum lipids have a recognized association with atherogenesis, an important class of antiatherosclerotic agents are those with serum lipid-modifying effects. Serum lipids implicated in atherogenesis include serum cholesterol, serum triglycerides, and serum lipoproteins.

With respect to serum lipoproteins, at least three different classes of these substances have been characterized: high density lipoproteins (HDL's), low density lipoproteins (LDL's), and very low density lipoproteins (VLDL's). HDL's are often referred to as alphalipoproteins, while LDL's and VLDL's are referred to as betalipoproteins. The enhancement to HDL levels (hyperalpha-lipoproteinemic activity) is postulated to have direct antiatherosclerotic effects. See Eaton, R. P., J. Chron. Dis. 31:131-135 (1978). In contrast, agents which reduce serum LDL's and serum VLDL's (hypobetalipoproteinemic agents) are also associated with antiatherogenic effects. See Haust, M. D., "Reaction Patterns of Intimal Mesenchyme to Injury and Repair in Atherosclerosis," Adv. Exp. Med. Biol. 43:35-57 (1974), which postulates that serum LDL is a factor in atherosclerotic lesion formation.

A large number of pyrrolizidine alkaloids and related structures are known in the literature: see the chapters on Pyrrolizidine Alkaloids in the review monographs "The Alkaloids", Vol. 1-12, The Chemical Society, Burlington House, London, 1971-82. These have been isolated from plants and insects. None of these have been reported to have lipid-altering or antiatherosclerotic activity, although they are generally associated with a larger number of toxic and pharmacologic effects. See, C. C. J. Culvenor, D. T. Downing and J. A. Edgar, "Pyrrolizidine Alkaloids as Alkylating and Antimitotic Agents", Ann. N.Y. Acad. Sci., 1969, 163, 837-847; E. K. McLean, "The Toxic Actions of Pyrrolizidine (Senecio) Alkaloids", Pharmacol. Rev., 1970, 22, 429-483; and more recently, the brief review by R. J. Huxtable in Gen. Pharmacol., 10:159 (1979). The biology of pyrrolizidines is also discussed in Culvenor, et al., Chem.-Biol. Interactions, 12:299-324 (1976).

Numerous fused ring systems containing a nitrogen atom are known, e.g., 2-5 membered ring systems (pyrrolizidines), 6 member-5 member ring systems (indolizidine type) and 2-6 membered ring systems (quinolizidine type). See, "The Alkaloids," supra. Certain pyrroletype fused ring systems which contain an enamide function are known and are naturally occurring, Id.

PRIOR ART

Sumoto, et al., J. Heterocyclic Chem. 18:413 (1981) discloses a delta-1,8-dehydropyrrolizidine compound. No use is disclosed for this compound. Cheng, et al., J. Amer. Chem. Soc. 103:2090 (1981) discloses certain fused 5-6 membered and 6—6 membered ring systems which are prepared by a Diels-Alder type reaction. By virtue of their method of synthesis the compounds disclosed therein all have a six-membered olefin ring. No uses are disclosed for these compounds. LaLonde, et al., in J. Org. Chem. 45:3664-3671 (1980) inferred the presence of certain methyl-indolizidones as intermediates for the preparation of certain nuphar indolizidine alkaloids. Finally, Buchs, et al., J. Org. Chem. 47:719 (1982) discloses (E)-5-hydroxypyrrolizidin-3-one, as well as the 5-methoxy and 5-ethoxy derivatives thereof, as intermediates.

SUMMARY OF THE INVENTION

The present invention particularly provides:
(1) a compound of the Formula I, or a mixture of optical isomers thereof, wherein R is
  (a) hydrogen,
  (b) $C_1-C_8$ alkyl, or
  (c) $C_3-C_{10}$ cycloalkyl; and
  wherein n is 1 or 2;
(2) a compound of the Formula II, or a mixture of racemates thereof, wherein R is
  (a) hydrogen,
  (b) $C_1-C_8$ alkyl, or
  (c) $C_3-C_{10}$ cycloalkyl;
  wherein n is 1 or 2; and
  wherein q is 0 or 1; and
(3) a compound of the Formula III wherein R is hydrogen or methyl.

The carbon atom content of various hydrocarbon containing moieties is indicated by a prefix designating the minimum and maximum number of carbon atoms in the moiety, i.e., the prefix $C_i-C_j$ indicates a carbon atom content of the integer "i" to the integer "j" carbon atoms, inclusive. Thus, $C_1-C_3$ alkyl refers to alkyl of 1-3 carbon atoms, inclusive, or methyl, ethyl, propyl, and isopropyl.

With respect to the above, $C_1-C_8$ alkyl is methyl, ethyl, propyl, butyl, pentyl, hexyl, heptyl, octyl, and isomeric forms thereof.

Examples of cycloalkyl of 3 to 10 carbon atoms, inclusive, are cyclopropyl, cyclobutyl, cyclopentyl, cyclohexyl, cycloheptyl, cyclodecyl, cyclopropylmethyl, cyclobutylmethyl, cyclopentylmethyl, cyclohexylmethyl, cycloheptylmethyl, 1- or 2-cyclopropylethyl, 1- or 2-cyclobutylethyl, 1- or 2-cyclopentylethyl, 1- or 2-cyclohexylethyl, 1-, 2-, 3- or 4-methylcyclohexyl, (bicyclo[3.1.1]hept-2-yl)methyl, and 6,6-dimethyl-(bicyclo[3.1.1]hept-2-yl)methyl.

Formulas I contains an asymmetric carbon. Thus, Formulas I is meant to encompass the pure optical isomers of these compounds as well as mixtures of isomers thereof. Formula II can contain up to 3 chiral centers and the wavy line is meant to indicate either stereochemical configuration at that position. Thus, all of the possible racemates are included in Formula II.

Numerous animal models have been developed for assessing antiatherogenic activity. Principal among these are models for assessing hypobetalipoproteinemic activity in the rat, antiatherosclerotic activity in the Japanese quail, and lipoprotein modifying activity in the monkey. For a description of the operation of the hypobetalipoproteinemic rat model, refer to the known methods of Schurr, P. E., et al., "High Volume Screening Procedure for Hypobetalipoproteinemia Activity in Rats", Adv. Exp. Med. Biol. 67: Atherosclerotic Drug Discovery, pp. 215–229, Plenum Press (1975). For a description of the Japanese quail model, see Day, C. E., et al., "Utility of a Selected Line (SEA) of the Japanese Quail (Coturnic Coturnix japonica) for the Discovery of New Anti-Atherosclerosis Drugs", Laboratory Animal Science 27:817–821 (1977). Testing is done in SEA Japanese quail fed a normal diet ("normal quail assay") and an atherogenic diet ("athero quail assay").

A suitable primate model for assessing antiatherosclerotic activity of chemical compounds is found in the cynomolgus monkey. In these animals base-line values for VLDL's, LDL's, and HDL's can be determined by controlling diet over a period of several weeks and sampling plasma daily. After establishing control values, the effects of drug treatment are assessed by administering by gavage with a predetermined series of doses of test compounds for a similar period (e.g., two weeks).

Compounds of the present application have been evaluated in one or more of these tests. In these tests, 1,2,7,7a-tetrahydro-3H-pyrrolizin-3-one (Example 1) has been shown to be the most effective overall, exhibiting a minimum effective dose in the monkey lipoprotein assay of less than 20 mg/kg/day. This compound also exhibits a minimum effective dose of approximately 6 mg/kg/day in the rat lipoprotein assay, a minimum effective dose of approximately 6 in the normal quail assay, and a minimum effective dose of 25–100 in the athero quail assay. 1,2,7a-tetrahydro-7a-methyl-3H-pyrrolizin-3-one (Example 3) exhibits a minimum effective dose of approximately 3 in the normal quail assay.

The patients susceptible to the development of atherosclerotic diseases and the untoward consequences thereof are particularly those physically asymptomatic patients manifesting one or more risk factors known to predispose one to disease development. Such risk factors are: high serum cholesterol and serum triglycerides, hypertension, obesity, diabetes, and genetic predisposition. Patients manifesting two or more risk factors are deemed to be especially susceptible to atheorsclerotic diseases. These compounds all exhibit pronounced oral pharmacologic activity. Accordingly, in using these compounds for the treatment of atherosclerosis, an oral route of administration, either by conventional oral dosage forms or by mixture with food, represents the preferred method of their systemic administration. Alternatively, however, these compounds may be administered by other convenient routes of administration whereby systemic activity is obtained. These other routes of administration would, accordingly, include rectal, vaginal, buccal, intramuscular, subcutaneous, intravenous, and like routes.

In humans, the preferred route of administration is oral, in the form of capsules or tablets containing the drug.

The patient or animal being treated must be given periodic doses of the drug in amounts effective to reduce atherogenic serum lipoproteins (e.g., betalipoproteins) or selectively enhance levels of antiatherogenic serum lipoproteins (e.g., enhancing alphalipoprotein levels, while suppressing, or at least unaffecting, betalipoprotein levels). Such effective dosages are readily determined by methods known in the art. For example, small daily doses of the drug (e.g., 50–100 mg) may be administered initially with higher succeeding doses until levels of atherogenic or antiatherogenic serum lipoproteins are favorably affected. By this regimen, a compound is administered initially at doses as low as about 10 mg per patient per day, with increasing doses up to about 200 mg per patient per day. In the event the antiatherogenic response in a patient being treated at a dose of 200 mg per day is insufficient, higher doses are also utilized to the extent tolerance permits further increases in dose.

While the preferred dosage regimen is with single daily dosing of patients, also preferred for obtaining more uniform serum levels of drug are multiple dosages per day (e.g., up to 4–6 times daily). Accordingly, when 4 daily doses of drug are to be administered, each such dose may be about 50 mg per patient per dose (200–300 mg per patient per dose), or higher depending on tolerance.

Similar doses are employed in non-human mammals, e.g., 1–5 mg/kg/day.

The compounds in accordance with the present invention are all useful as antiatherosclerotic agents. Thus these compounds are employed by methods known in the art for the use of lipid-altering compounds in the treatment and prevention of atherosclerosis. Accordingly, compounds of Formula I are employed in humans and in nonhuman mammals at doses from about 0.5–100 mg/kg/day and preferably 0.1–50 mg/kg/day orally. These compounds are used orally in conventional oral dosage forms, including capsules, tablets, and pharmaceutically acceptable liquids. When routes of administration employed, equivalent dosages and used.

Compounds of Formula I are also useful as food or feed additives whereby the ingestion of food or feed by the mammal being treated results in an effective oral dose of the compound.

Preferred among the compounds of Formula I are those wherein R is hydrogen or methyl and n is 1. Thus, 1,2,7,7a-tetrahydro-3H-pyrrolizin-3-one (Example 1) and 1,2,7a-tetrahydro-7a-methyl-3H-pyrrolizin-3-one (Example 3) are the most preferred compound of this invention.

The novel compounds of the Formula II and III are useful as intermediates to prepare the Formula I compounds.

The novel compounds disclosed in the present specification are all prepared by methods described in Charts A and B.

With respect to the charts, R and n are as defined above in the specification. In the Charts, the compounds of the Formulas A-1, A-2, A-3 and B-7 and some of the A-4 compounds are known and are available commercially or can be prepared by methods described in the literature cited under "Prior Art." See, also, U.S. Pat. Nos. 2,342,119 and 2,390,918 for the preparation of Formula A-1 type compounds.

Chart A depicts a method for preparing compounds of the present invention wherein n is 1. The conversion of the A-1 compound to the A-3 compound is undertaken by methods well-known in the art, see, e.g., Leonard, et al., J. Am. Chem. Soc. 69:690–692 (1974). Reduction of the dilactam of the Formula A-3 by means known in the art (see, e.g., Buchs, et al., J. Org. Chem. 47:719 (1982) which employs lithium aluminum hydride (LAH) in tetrahydrofuran (THF)) yields the Formula A-4 carbinol lactam. This compound is then treated with methanethiol to yield the Formula A-5 compound. This A-5 compound is treated with m-chloroperbenzoic acid or sodium periodate to yield the Formula B-12 methylsulfinyl compound. This compound is heated in a pyridine solution to yield the Formula I product wherein n is one.

Chart B depicts a method for preparing compounds of this invention wherein n is one or two. In Chart B by methods known in the art, see, e.g., House, "Modern Synthetic Reactions", pp. 595–623 (Benjamin 1972), the Formula B-7 is converted to the Formula B-8 aldehyde. The aldehyde compound of the Formula B-8 is treated with ethylene glycol and p-toluene sulfonic acid to yield the Formula B-9 acetal. (See Preparation 1). This compound is treated with hydrogen in the presence of a platinum oxide or Raney nickel catalyst, catalyst in methanol (see Preparation 2) to yield the Formula B-10 compound. This compound is treated with p-toluene sulfonic acid (PTSA) and methanethiol to yield the Formula B-11 compound. (Note that this compound contains the A-5 compounds within its scope.) This compound is converted to the final products by the methods described above with regard to Chart A (see also, e.g., Preparation 4 and Example 1).

A preferred, procedure for converting the Formula A-3 diketone to the Formula A-5 methylthio compound is depicted in Chart C. The diketone of Formula A-3 is treated wth methane thiol in the presence of a trace of acetic anhydride followed by sodium borohydride to yield the Formula A-5 compound and the Formula C-1 dithioketal byproduct. (See Preparation 14.) Recovery of the Formula C-1 byproduct may be accomplished by treating it with p-toluenesulfonic acid (PTSA) in acetonitrile with heating (see Preparation 15) to convert the Formula C-1 dithioketal compound to the Formula A-5 intermediate.

Thus, in accordance with the procedure of Charts, each of the various Formula I and Formula II compounds provided in the present disclosure is prepared.

DESCRIPTION OF THE PREFERRED EMBODIMENTS

The preparation of the novel compounds disclosed herein is more readily understood by the operation of the following examples:

Preparation 1

γ-Nitro-1,3-dioxolane-2-pentanol, Acetate

Refer to Chart B (Conversion of B-7 to B-9).

A solution of 4-nitro-7-oxo-heptanoic acid, methyl ester ($CH_3OCOCH_2CH_2CH(NO_2)CH_2CH_2CHO$) (22.2 g; 0.113 mol), ethylene glycol (7.76 g; 0.125 mol), and PTSA (0.10 g) in toluene (250 ml) was heated at reflux for 20 hours with a Dean-Stark trap. The solvent was removed in vacuo to afford an oil. This was distilled to afford: 1.93 g of titled crystals with a melting point of 120°-2° C.

Analysis calcd for $C_{10}H_{17}NO_6$: C, 48.57; H, 6.93; N, 5.67 Found: C, 48.77; H, 7.31; N, 5.27.

Mass spectrum calcd: m/e=246 (M+ −1), Found: m/e=246 (M+ −1).

TLC ($SiO_2$): Rf=0.60 (ethylacetate) D°($I_2$)

NMR ($CDCl_3$, δ): 1.50–2.60, 3.70 and 4.95.

IR ($cm^{-1}$): 1740, 1550, 1365, 1440, 1205, 1175, 1145 and 1030.

PREPARATION 2

5-[2-(1,3-Dioxolan-2-yl)ethyl]-2-pyrrolidinone

Refer to Chart B (Conversion of B-9 to B-10).

Preparation 1 (16.5 g; 0.067 mole), platinum oxide (5.0 g; .33 mole %), and methanol (100 ml) were combined in a hydrogenation bottle. The bottle was pressurized to 50 lbs of hydrogen and shaken for 18 hours. The bottle was removed from the shaker and the contents were filtered and evaporated at 50° C., affording 15.4 g of crude product. 100% of the theoretical amount of hydrogen was taken up.

The crude product was distilled at 0.01 mm Hg and the pure lactam acetal boiled from 146°-148° C. The distilled material set solid on standing and 11.6 g of off-white solid was recrystallized from 50 ml of 80% ethyl acetate/hexane. 7.2 g (58% yield) of analytical material was obtained after drying the crystals in vacuo overnight at 30°. A further 1.1 g (9%) of material which was pure by NMR was obtained by recrystallization of mother liquors. Both crops melted at 88°–90°.

Anal. calcd. for $C_9H_{15}NO_3$: C, 58.36; H, 8.10; N, 7.56, Found: C, 58.54; H, 7.87; N, 7.87.

Mass spectrum: Parent ion at m/e 185 others at m/e 84, 73, 97, 45, 41, 142, 69, 28, 56, and 85.

TLC ($SiO_2$): Rf=0.1 (EtOAc) ($I_2$)

NMR ($CDCl_3$, δ): 1.6–1.8, 2.30, 3.7, 3.9 4.9, and 7.15.

IR ($cm^{-1}$): 3180, 3080, 1690, 1150, 1110, 1045, 945, 895 and 805.

UV (ethanol): end abs.

PREPARATION 3

Hexahydro-5-methylthio-3H-pyrrolizin-3-one
(Formula II, R is hydrogen, n is 1, q is 0).

Refer to Chart B (Conversion of B-10 to B-11.).

A solution of Preparation 2 (9.00 g; 48.6 mmol) and p-toluene sulfonic acid (1.50 g) in methanethiol (225 g) was placed in a freezer (−8° C.) for 11 days. The reaction was then removed from the freezer and the $CH_3SH$ was removed in vacuo to afford 13.46 g of a thick oil. TLC analysis showed a weak spot at the origin and strong spots at Rf0.20 and 0.30 (ethylacetate) ($I_2$). This mixture was chromatographed using HPLC with ethyl acetate as the eluant. The fractions with a Rf=0.30 were combined and the solvent was removed in vacuo to afford 4.04 g (49%) of the titled product.

Anal. Calcd for $C_8H_{13}NOS$: C, 56.11; H, 7.65; N, 8.18, Found: C, 55.72; H, 7.74; N, 7.94.

Mass spectrum: calcd: m/e=171 (M+), Found: m/e=171 (M+).

TLC ($SiO_2$): Rf=0.30 (ethyl acetate) ($I_2$)

NMR ($CDCl_3$, δ): 1.10–3.00, 3.80–4.40 and 4.95–5.30.

IR ($cm^{-1}$): 1695, 1395, 1295, 1280, 1190 and 1175.

UV: end abs.

The fractions with a Rf=0.20 were combined and the solvent was removed in vacuo to afford 5.56 g (51%) of I.

Analysis: calcd for $C_9H_{17}NOS_2$: C, 49.27; H, 7.81; N, 6.38; S, 29.23. Found: C, 49.00; H, 8.00; N, 6.13.

Mass Spectrum: Calcd: 219.0754, Found: 219.0752.

TLC ($SiO_2$): Rf=0.20 (ethyl acetate) ($I_2$)

NMR ($CDCl_3$, δ): 1.60–1.90, 3.10, 2.10–2.55, 3.30–3.80, and 7.35.

IR ($cm^{-1}$): 1695, 1395, 1295, 1280, 1190, and 1170.

UV: end abs.

PREPARATION 4

Hexahydro-5-methylsulfinyl-3H-pyrrolizin-3-one
(Formula II, R is hydrogen, n is one, q is one).

Refer to Chart B (conversion of B-11 to B-12).

Sodium periodate (2.14 g; 10.0 mmol) was dissolved in water (100 ml) and the compound of Preparation 3 (1.65 g; 9.65 mmol) dissolved in methanol (100 ml) was added with stirring at ambient temperature. After 1.25 hours the reaction mixture was taken to dryness in vacuo, extracted with chloroform (250 ml), filtrate was dried (sodium sulfate) and the solvent was removed in vacuo to afford 1.67 g (93%) of the titled product as an oil.

Anal. calcd. for: $C_8H_{13}NO_2S$: C, 51.32; H, 7.00; N, 7.48; S, 17.12 Found: C, 50.95; H, 7.35; N, 7.14; S, 17.18

Mass Spectrum: Calcd: m/e=187 (M+) Found: m/e=187 (M+).

TLC ($SiO_2$): Rf=streck from origin to 0.15 (ethyl acetate) ($I_2$)

NMR ($CDCl_3$, $\delta$): 1.20–3.00, 3.70–4.40 and 4.50–5.90.

IR ($cm^{-1}$): 1695, 1395, 1295 and 1050.

UV: end abs.

Alternatively, the titled product may be prepared as follows: Preparation 3 (10.26 g; 0.6 mole) was dissolved in 300 ml of methylene chloride. m-Chloroperoxybenzoic acid (11.84 g; 0.07 mole) was dissolved in 300 ml of methylene chloride and this solution was added with magnetic stirring to the reaction mixture dropwise, over 2.5 hrs. The reaction was allowed to stir for 0.5 hr after the addition was complete. Tlc indicated a complete reaction. Ammonia gas was bubbled through the solution to precipitate the benzoic acid(s) as ammonium salt(s). The salts were removed by filtration and 7.2 g of anhydrous magnesium sulfate was added before the solvent was removed on a rotary evaporator under house vacuum at 30° C.

EXAMPLE 1

1,2,7,7a-Tetrahydro-3H-pyrrolizin-3-one (Formula I: R is hydrogen, n is 1)

Refer to Chart B (conversion of B-12 to I).

A solution of Preparation 4 (2.00 g; 10.7 mmol) in pyridine (15 ml) was heated at 100° C. with stirring for 20 hours. The reaction mixture was cooled and the solvent was removed in vacuo to afford a dark oil. This was diluted with methylene chloride (1 ml) and chromatographed using high pressure liquid chromatography (HPLC) on a Lobar size C column with ethyl acetate. The flow rate was 3.5 ml/min., collecting 7 ml fractions. The fractions containing the compound with an Rf=0.30 (ethyl acetate) (U.V.) were combined and the solvent was removed in vacuo to afford 0.95 g of a light brown solid. This was sublimed at 45°/0.05 mm to afford 0.81 g (67%) of titled product: mp. 65°–6°.

Anal. calcd. for $C_7H_9NO$: C, 68.27; H, 7.37; N, 11.37 Found: C, 68.04; H, 7.38; N, 11.63.

Mass spectrum: Calcd.: m/e=123 (M+) Found: m/e=123 (M+).

High Resolution: Calcd: 123.0684 Found: 123.0687

TLC ($SiO_2$): Rf=0.30 (ethyl acetate) (U.V.)

NMR ($CDCl_3$, $\delta$): 1.50–3.05, 4.00–4.75, 5.30–5.50 and 6.50–6.60.

PREPARATION 5

5-Nitropentanoic acid, methyl ester

Refer to Chart B (preparation of Formula B-7 compound).

Silver nitrite (28.8 g; 0.15 mole) and anhydrous ether (50 ml) were stirred at 0° for the dropwise addition of methyl bromovalerate over 2 hours. The suspension was stirred at 0° for 24 hours, then at room temperature for 40 hours. The crude reaction mixture was filtered through Celite and the ethereal filtrate was evaporated at 40° in vacuo to afford 18.1 g of oily product. 10 ml of water was added to decompose the nitrite ester by-product while evaporating on a rotary evaporator at 60°. The crude product (16.2 g) was applied to an E. Merck HPLC column, size "C". Elution with 2.5% ethyl acetate/methylene chloride afforded 9.9 g of analytically pure U-62,990 (38% yield).

Anal. Calcd. for $C_6H_{11}NO_4$: C, 44.71; H, 6.88; N, 8.29, Found: C, 44.76; H, 6.82; N, 8.61.

Mass Spectrum: No M+ seen; (M—$CH_3$)+ at 130

NMR ($CDCl_3$, $\delta$): 4.5, 3.7, and 1.35–2.7.

IR ($cm^{-1}$): $\nu_{CO}$=1735, others at 1555, 1435, 1385, 1375, 1200, and 1165.

UV (ethanol): end absorption.

PREPARATION 6

Methyl 5-nitro-8-ethylenedioxyoctanoate

Refer to Chart B (conversion of B-7 to B-8).

Preparation 5 (4.83 g; 0.03 mole), methanol (25 ml), and potassium fluoride dihydrate (0.3 g; 0.003 mole) were stirred at 40°. A solution of acrolein (1.7 g; 0.03 mole) in methanol (10 ml) was added dropwise such that half of the solution was added over 0.5 hours. The remaining acrolein solution was diluted to 10 ml with methanol and added over 1.0 hour, diluted to 50 ml with methylene chloride, and applied to a column of 25 g of silica gel solvated with methylene chloride. Elution with methylene chloride afforded fractios which were evaporated to yield 6.1 g of crude product. The crude oil was dissolved in toluene (100 ml). p-Toluenesulfonic acid (1 crystal; catalytic amount) and ethylene glycol (3.1 g; 0.05 mole) were added and the incomplete solution was refluxed for 1 hour using a Dean-Stark trap to remove the water formed. The crude product was filtered through 75 g of silica gel and eluted with methylene chloride until no more material came off. Evaporation of the solvent at 40° in vacuo afforded 6.4 g of crude U-62,991. The crude oil was distilled at 0.01 torr and the product (3.9 g; 56% yield) collected at 137°–140°.

Anal. calcd for $C_{11}H_{19}NO_6$: C, 50.56; H, 7.33; N, 5.36, Found: C, 50.65; H, 7.28; N, 5.14.

Mass spectrum: Exact mass calcd m/e=261.1193, Found m/e=261.1212.

NMR ($CDCl_3$, $\delta$): 4.9, 4.8–4.25, 3.9, 3.65, and 1.4–2.6.

IR ($cm^{-1}$): $\nu_{CO}$=1740; others at 1550, 1440, 1365, 1200, 1176, 1145 and 1035.

UV (ethanol): End absorption.

PREPARATION 7

6-(3-Ethylenedioxy-1-propyl)-2-piperidinone

Refer to Chart B (conversion of B-9 to B-10).

Preparation 6 (15.0 g, 0.064 mole), Platinum oxide (4.57 g; 0.02 mole), and methanol (150 ml) were combined under nitrogen in a hydrogenation bottle. The bottle was evacuated, purged with nitrogen, and pressurized with hydrogen to 50 psi. After shaking for 25 hours, the catalyst was removed by filtration and the solvent was evaporated to afford 13.2 g of oil which solidified on standing. The product was dissolved in 20% hexane in toluene (20 ml), allowed to crystallize at room temperature for 1 hour, then at −5° for 4 hours. Filtration of the crystals and drying in vacuo for 18 hours afforded 7.5 g of crystals. Recrystallization of a 2.5 g sample afforded 1.25 g of analytically pure material, mp 93.5°–95° (approximately 30% yield).

Anal. Calcd. for $C_{10}H_{17}NO_3$: C, 60.28; H, 8.60; N, 7.03 Found: C, 60.08; H, 8.50; N, 6.80.

Mass spectrum: M+ at m/e 199

NMR ($CDCl_3$, δ): 7.05, 4.9, 3.9, 3.2–3.7, and 1.3–2.6.

IR ($Cm^{-1}$): $\nu_{CO}=1665$, $\nu_{NH}=3180, 3080$; others at 1415, 1315, 1195, and 1135.

UV (ethanol): end absorption.

PREPARATION 8

1a-Homo-5-methylthio-pyrrolizidin-3-one (Formula II: R is hydrogen, n is 2, q is zero)

Refer to Chart B (conversion of B-10 to B-11).

Preparation 7 (5.9 g; 0.03 mole) and p-toluenesulfonic acid (0.25 g; catalytic amount) were melting at 100° in a 25 ml round bottom flask under nitorgen. The molten reactants were stirred magnetically and a dry ice condenser was introduced above the flask. Methanethiol was condensed 1 or 2 drops at a time into the reaction vessel, allowing 5 minutes for the reaction to take place. Additional thiol was added dropwise until the starting mateiral had disppeared by TLC (10% isopropanol/-methylene chloride). 6.3 g of crude product was combined with 13.7 g of material synthesized in the same manner and purified by HPLC using three 47×450 mm Michel-Miller columns in series. Elution with 2.5% isopropanol in methylene chloride afforded 7.8 g of analytically pure material, plus a 6.4 g fraction which contained a small amount of a less polar impurity. (Yield is approximately 78%).

Anal. Calcd. for $C_9H_{15}NOS$: C, 58.33; H, 8.16; N, 7.56; S, 17.50 Found: C, 58.51; H, 8.34; N, 7.42; S, 17.42

Mass spectrum: M+ at m/e 185; M+—$SCH_3$ at 138

NMR ($CDCl_3$, δ): 5.5, 3.6, 1.0 to 2.5 and 2.4.

IR ($Cm^{-1}$): $\nu_{CO}-1645$

UV (ethanol): End absorption.

EXAMPLE 2

6,7,8,8a-tetrahydro-5(1H)Indolizinone (Formula I: R is hydrogen, n is 2)

Refer to Chart B (conversion of B-11 to B-12 to I).

Preparation 8 (5.35 g; 0.029 mole) was dissolved in methylene chloride (100 ml) and the solution was stirred at 0°. m-Chloroperbenzoic acid (5.73 g of 85% purity; 0.033 mole) was dissolved in methylene chloride (100 ml) and the solution was added dropwise over 1 hour to the reaction mixture. After stirring 1 hr ammonia was bubbled through the reaction mixture until precipitation was complete, then the chalky white precipitate was removed by filtration through Celite into a flask containing sodium bicarbonate (0.5 g) and magnesium sulfate (1.0 g). The solvent was removed in vacuo at 40°, freshly distilled pyridine (5 drops) was added, and the mixture was stirred at 130° overnight. The product was evaporated at 45° in vacuo for 1 hour, then the crude olefin was dissolved in 50 ml of methylene chloride and filtered through Celite. The solution was evaporated to a volume of 10 ml and was applied to a 22×300 mm and 37×350 mm Michel-Miller HPLC column equilibrated with 5% isopropanol in methylene chloride. Elution with the same solvent afforded 3.2 g of slightly impure material. The product was applied to 37×350 mm and 47×450 mm columns in series. Elution with acetonitrile afforded 2.6 g of pure titled product (65% yield).

Anal. Calcd. for $C_8H_{11}NO$: C, 70.04; H, 8.08; N, 10.21; Found: C, 70.37; H, 8.48; N, 10.19;

Mass spectrum: M+ at 137; others at 80, 68, 39

NMR ($CDCl_3$, δ): 7.0, 5.3, 3.95 and 1.3–3.0.

IR ($Cm^{-1}$): $\nu_{CO}-1643.5$

UV (ethanol): $\nu=244$ $\epsilon=5,850$.

PREPARATION 9

4-Nitro-pentanoic acid, methyl ester

Refer to Chart B (Preparation of B-7).

Methyl acrylate diluted with 150 ml of nitroethane (500.0 g, 5.80 moles) was added dropwise to 900 g (11.90 moles) of nitroethane and potassium fluoride dihydrate (45.7 g, 0.485 mole) at 40° C. Addition was accomplished over a 5 hour period. After the addition the reaction was stirred at 40° C. for 2 hours. The solid which formed was filtered. The solvent was removed under reduced pressure to yield 849 g of oil. The oil was dissolved in 1.4 L of methylene chloride and placed on a 1 kg column of silica gel. The column was developed with methylene chloride and 8 fractions (1 L/fraction) were collected. Removal of the solvent from these fractions gave 623 g of a light green oil. This oil was distilled and three fractions were collected, fraction I, (boiling point (b.p.) is 30°–80° C. at 10 mm) gave 60 g, fraction II, (b.p. is 95°–96° C. at 3 mm); fraction III, (b.p. 95°–96° (at 3 mm) gave 221 g. Fractions II and III were combined to yield 468 g of the titled compound (50% yield). The b.p. is 95°–96° C. at 3 mm.

NMR ($CDCl_3$, δ) 1.55, 2.0–2.5, and 4.65.

PREPARATION 10

Methyl-4-methyl-4-nitro-6-ethylenedioxy heptanoate

Refer to Chart B (Conversion of B-7 to B-9).

The nitro compound of Preparation 9 (5.0 g 0.031 mole) was added to 10 ml of methanol which contained 0.30 g, (0.0032 mole) of potassium fluoride dihydrate at 40° C. Acrolein (1.74 g, 0.0316 mole) in 5 ml of methanol was then added to the above suspension over a 0.5 hour period. The reaction was heated to 60° C. for 72 hours. An additional 1.0 ml of acrolein was added and the reaction was heated at 60° C. for 6 additional hours. The solvent was removed under reduced pressure. The yellow oil which remained was placed on a 35 g column of silica gel. The column was eluted with methylene chloride and 10 fractions (100 ml/fraction) were collected. Removal of the solvent from these fractions gave 4.5 g of oil. This oil was analyzed by gas chromatograph (3% Se 30 column, Time 1=4.0 min at 75° C., Time 2=5.0 min at 250° C.). The purity was shown to be 65%.

The partially purified aldehyde was placed into 50 ml of toluene which contained (20 mg, 0.0016 mole) of γ-toluenesulfonic acid. Ethylene glycol (11.25 g, 0.03 mole) was added. The reaction was brought to reflux for 3 hours. The reaction was cooled to room temperature and the solvent removed under reduced pressure. The oil was then distilled under reduced pressure and gave (1.0 g) of the titled product having a b.p. of 156°-160° C. at 1.0 mm Analysis Calcd. for $C_{11}H_{17}NO_6$: C, 50.56; H, 7.33; N, 5.35. Found: C, 51.13; H, 7.60; No, 5.32.

Mass spectum peaks at 261, 153, 139, 121, 93, 86, 74, 73, 55, 45 and 41.

Infrared ($\lambda$max, mull) 2954, 2887, 1738, 1538, 1348, 1439, 1202, 1176, 1142, and 1034 cm$^{-1}$.

PREPARATION 11

5-[(3-Ethylenedioxy-1-propyl)]-5-methyl-2-pyrrolidinone

Refer to Chart B (conversion of B-9 to B-10).

The nitro compound of Preparation 10 (10.0 g, 0.038 mole) was dissolved in 150 ml of absolute ethanol which contained (10.3 g) of Raney-nickel (Degaussa Lot 1018, Type 113 RW). The reaction was then hydrogenated at room temperature for 22 hours. The catalyst was filtered by gravity. The solvent was removed under reduced pressure to yield 8.3 g of oil. The oil was placed into 100 ml of toluene and heated to 90° C. for 3 hours. The solvent was removed under reduced pressure to yield an oil. The oil was dissolved in 5% methanol-methylene chloride and placed on a 150 g column of silica gel. The column was developed with 5% methanol-methylene chloride and 27 fractions were collected. Fractions 4–12 (200 ml/fraction) were combined on the basis of TLC data (1"×4" silica gel plates, 5% methanol-methylene chloride as developing agent). Removal of the solvent gave 4.5 g of product. This material was dissolved in 50 ml of ether and than diluted with 150 ml of petroleum ether. The solid which formed was filtered to give 4.3 g of titled product. (57%) The mp is 74°-77° C.

Analysis calcd. for $C_{10}H_{17}NO_3$: C, 60.28; H, 8.60; N, 7.03, Found: C, 60.18; H, 8.60; N, 6.87.

Mass spectrum reveals peaks at 199, 156, 122, 101, 99, 98, 97, 82, 73, 55, and 45.

NMR (CDCl$_3$, $\delta$) peaks at 1.2, 1.6-2.4, 3.85, 4.8 and 6.5.

Infrared ($\lambda$max, mull): 3180, 3113, 3075, 1680, 1682, 1130, 1027, 980 and 882 cm$^{-1}$.

PREPARATION 12

Hexahydro-7a-methyl-5-methylthio)-3-H-pyrrolizin-3-one

Refer to Chart B (conversion of B-10 to A-5).

The acetal of Preparation 11 (3.7 g, 0.086 mole) was placed in a round bottomed flask along with (0.2 g, 0.0010 mole) of p-toluene sulfonic acid. Methanethiol gas was then added to the reaction under a dry ice condenser. The reaction was heated to 100° C. for 1.5 hours. During this time the flow of mercaptan was continued. The reaction was cooled to room temperature and diluted with 100 ml. of 10% ethylacetate-methylene chloride. This mixture was then placed onto a 250 g column of silica gel. The column was developed with 10% ethylacetate-methylene chloride. Twenty five fractions were collected. Fractions 8–21 (200 ml/fraction) were combined and gave 1.7 g of oil after removal of the solvent. The oil was dissolved in 20 ml of petroleum ether and cooled in a dry ice acetone bath. The solid which formed was filtered to give 1.4 g (41%) of titled product. The mp is 44°-46° C.

Analysis calcd. for $C_9H_{15}NOS$: C, 58.36; H, 8.16; N, 7.56; S, 17.28 Found: C, 58.17; H, 8.11; N, 7.63; S, 17.35

Mass spectrum peaks at 185, 139, 138, 96, 95, 94, 93, 67, 55, 41, 39.

NMR (CDCl$_3$, $\delta$) peaks at 1.5, 1.6-2.1, 2.35, 2.4-3.0 and 5.1.

Infrared ($\nu$max, mull) 1699, 1375, 1369, 1331, 1202, and 1181 cm$^{-1}$.

PREPARATION 13

Hexahydro-7a-methyl-5-(methylsulfinyl)-5H-pyrrolizin-3-one

Refer to Chart B (conversion of A-5 to B-12).

The thiomethyl compound 5 (4.2 g, 0.023 mole) was dissolved into 65 ml of methylene chloride. m-Chloroperoxybenzoic acid (85% pure, 4.589 g, 0.0265 mole) was dissolved in 65 ml of methylene chloride. This latter solution was then added dropwise to the thio compound over a 1.0 hour period. The reaction was then allowed to stir at room temperature (ice water bath) and anhydrous ammonia gas was bubbled into the reaction for 10 minutes. The solid which formed was filtered. The solvent was removed under reduced pressure to yield 4.6 g of yellow oil. The oil was dissolved in 50 ml of methylene chloride and 75 ml of hexane added. A highly crystalline solid developed and was filtered. This solid was dried overnight and gave 3.4 g. The solvent was removed from the filtrate and 700 mg of light yellow oil was isolated. The oil was triturated with ether and a solid formed (3 days). These solids were combined to give 3.70 g (80%) mp=88°-91° C.

Analysis calcd. for $C_9H_{15}NO_2S$: C, 53.71; H, 7.51; N, 6.96; S, 15.90. Found: C, 53.37; H, 7.54; N, 6.89; S, 15.75.

Mass spectrum reveals peaks at 185, 159, 138, 96, 95, 94, 93, 82, 67 and 55.41.

NMR (CDCl$_3$, $\delta$) peaks at 1.6-3.0 and 4.65.

EXAMPLE 3

1,2,7,7a-Tetrahydro-7a-methyl-3H-pyrrolizin-3-one (Formula I: R is methyl, n is 1)

Refer to Chart B (conversion of B-12 to I)

The sulfoxide of Preparation 13 (78 g, 0.039 mole) was slurried with 23 drops of pyridine magnesium sulfate (3.65 g, 0.030 mole), and sodium bicarbonate (2.43 g, 0.028 mole). This mixture was then heated to 130° C. for 18 hours. The reaction was cooled to room temperature, and then the reaction was diluted with 75 ml of ethyl acetate. This mixture was then placed on a column of silica gel (70–230 mesh) (400 g). The column was developed with ethyl acetate and 24 fractions (200 ml/fraction) were collected. Fractions 5–22 (200 ml/fraction) gave 4.4 g of impure olefin after removal of the solvent. This 4.4 g was dissolved in 20 ml of ethyl acetate and placed onto a Michel Miller column (47×450 mm) which was packed with silica gel (230–400 mesh). The column was developed with ethyl acetate and fractions 29–63 (40 ml/fraction) gave 2.7 g (51%) of titled compound as a light yellow oil.

In order to obtain a solid sample, 469 mg of the oil was dissolved in 4 ml of ether. Following this petroleum ether (200 ml) was added. The solution was cooled below room temperature and the solid which formed was filtered to give 200 mg of the titled product, with a mp of 29°-31° C.

Analysis calcd. for: C, 70.05; H, 8.08; N, 10.20. Found: C, 69.69; H, 8.30; N, 10.00.

Mass spectrum reveals peaks at 137, 122, 82, 81, 80, 55, 54, 42, 41, and 39.

NMR (CDCl$_3$, δ) peaks at 1.30, 1.8–3.1, 5.3 and 6.5.
Infrared (νmax, mull) 3092, 3080, 1710, 1597, and 1576 cm$^{-1}$.

PREPARATION 14

Hexahydro-5-(methylthio)-3H-pyrrolizin-3-one

Refer to Chart C (conversion of A-3 to A-5 and C-1).

The 1.0 g (7.1 mmoles) of the dilactam of the Formula A-3, wherein R is hydrogen (prepared as described in Leonard, J. Amer. Chem. Soc. 69:690 (1947) was placed in a 2-neck 100 ml flask under nitrogen. A dry ice condenser was then attached. Methane thiol was added until the substrate and mechanical stirrer were both covered. Following this sodium borohydride (0.5 g, 13.95 mm) was added. After 15 minutes at room temperature the reaction was diluted with aqueous hydrochloric acid (11.2 ml, 5M, 55.8 mm). The solvent was removed under reduced pressure and a solid was siolated. This solid was triturated with 3 30 ml portions of warm chloroform. The solvent was dried over sodium sulfate. Removal of the solvent gave 1.05 g of oil. The oil was dissolved in ethyl acetate (5 ml) and placed on a 2×300 mm Michel-Miller column. Elution of the column in 30 ml fractions with ethyl acetate produced (0.32 g) (26%) of the title product in fractions 8–11.

Mass spectrum reveals peaks at 171, 125, 124, 81, 80, 68, 55, 45, 41, and 39.

NMR (CDCl$_3$, δ) peaks were observed at 1.1–2.1, 2.25, 2.35–2.9, 4.15, and 5.1.

Continued elution of the column gave TLC dithioacetal (Formula C-1) in fractions 21–37. Removal of the solvent gave 0.4 g of the dithioacetal (25.6%) as a solid.

Mass spectrum reveals peaks at 219, 204, 172, 125, 124, 84, 81, 80, 55, and 41.

NMR (CDCl$_3$, δ) peaks were observed at 1.6–1.9, 2.10, 2.1–2.3, 3.6, and 7.0.

PREPARATION 15

Hexahydro-5-(methylthio)-3H-pyrrolizin-3-one from dithioacetal

A solution of a dithiacetal compound of the Formula C-1 wherein R is hydrogen (3.28 g; 15.0 mmol) and PTSA (0.15 g) in acetonitile (250 ml) was heated at reflux for 20 hours. TLC showed a weak spot at R$_f$=0.20 and strong spot at R$_f$=0.30 (ethylacetate, iodine) analysis. The solution was cooled and the solvent was removed in vacuo to afford an oil. This was chromatographed by HPLC using ethylacetate as the eluent. The fractions which contained material with an R$_f$=0.30 were combined and the solvent was removed in vacuo to afford 1.98 g (77%) of hexahydro-5-(methylthio)-3H-pyrrolizin-3-one.

TLC (silicon-dioxide): R$_f$—0.30 (ethylacetate, iodine) is consistent with the desired product.

FORMULAS

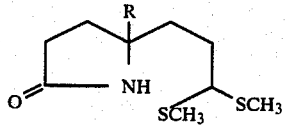

III

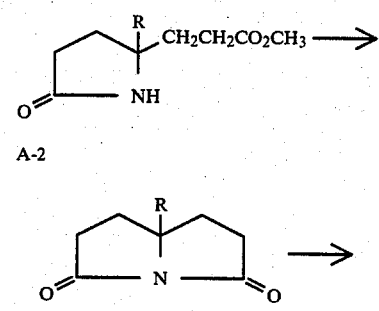

CHART A

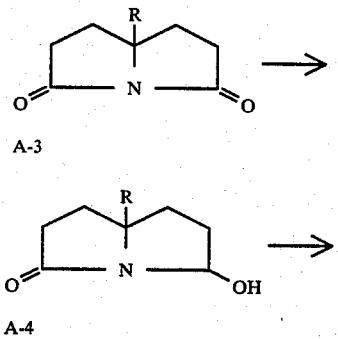

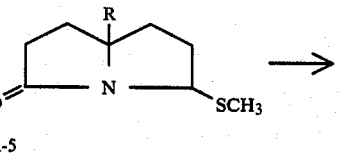

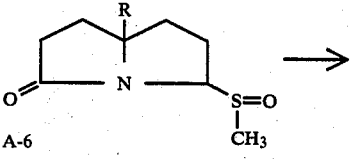

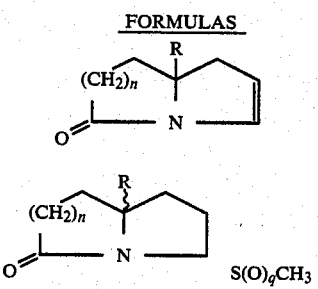

CHART B

H—C(R)(NO$_2$)—CH$_2$(CH$_2$)$_n$CO$_2$CH$_3$ ⟶

B-7

-continued
CHART B

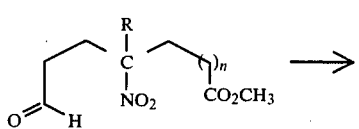

B-8

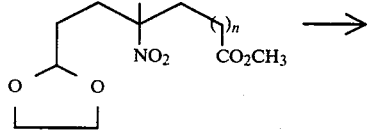

B-9

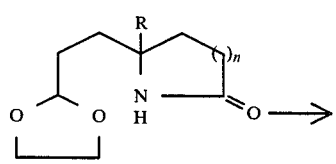

B-10

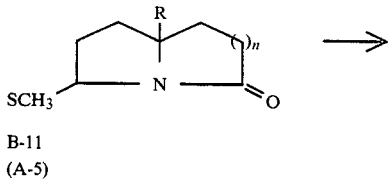

B-11
(A-5)

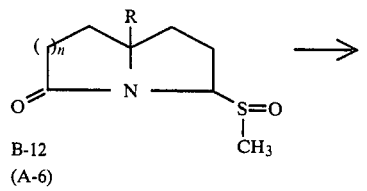

B-12
(A-6)

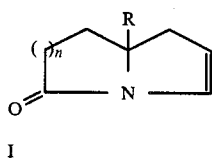

I

CHART C

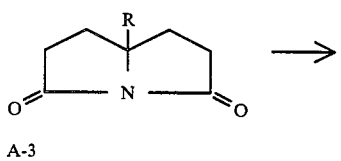

A-3

-continued
CHART C

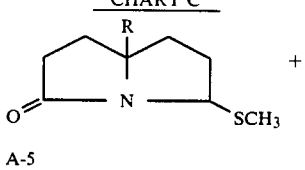

A-5

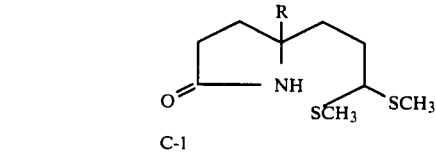

C-1

We claim:
1. A compound of the Formula I

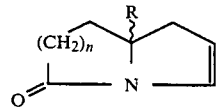 I wherein R is
(a) hydrogen,
(b) $C_1$–$C_8$ alkyl, or
(c) $C_3$–$C_{10}$ cycloalkyl; and
wherein n is 1 or 2.
2. A compound of the Formula II

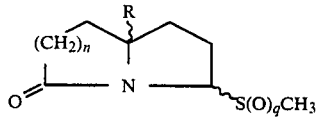 II wherein R is
(a) hydrogen,
(b) $C_1$–$C_8$ alkyl, or
(c) $C_3$–$C_{10}$ cycloalkyl;
wherein n is 1 or 2; and
wherein q is 0 or 1.
3. A compound of the claim 1, wherein R is hydrogen or methyl and n is one.
4. A compound of the claim 2, wherein R is hydrogen or methyl and n is one.
5. 1,2,7,7a-Tetrahydro-3H-pyrrolizin-3-one, a compound of claim 3.
6. Hexahydro-5-methylthio-3H-pyrrolizin-3-one, a compound of claim 4.
7. Hexahydro-5-methylsulfinyl-3H-pyrrolizin-3-one, a compound of claim 4.
8. 1a-Homo-5,6-didehydro-pyrrolizidin-3-one, a compound of claim 1.
9. 1a-Homo-5-methylthio-pyrrolizidin-3-one, a compound of claim 2.
10. 1a-Homo-5-methylsulfinyl-pyrrolizidin-3-one, a compound of claim 2.
11. 1,2,7,7a-Tetrahydro-7a-methyl-3H-pyrrolizin-3-one, a compound of claim 3.
12. Hexahydro-7a-methyl-5-methylthio-3H-pyrrolizine-3-one, a compound of claim 4.
13. Hexahydro-7a-methyl-5-methylsulfinyl-3H-pyrrolizin-3-one, a compound of claim 4.

* * * * *

UNITED STATES PATENT OFFICE
CERTIFICATE OF CORRECTION

Patent No. 4,581,462             Dated   8 April 1986

Inventor(s)   E.W. Yankee, et al.

It is certified that error appears in the above-identified patent and that said Letters Patent are hereby corrected as shown below:

Column 10, line 13, "(ethanol): $\nu=$" should read -- (ethanol): $\lambda=$ --.

Column 11, line 42, "($\lambda$max, mull)" should read -- ($\gamma$max, mull) --.
Column 12, line 5, "($\nu$max, mull)" should read -- ($\gamma$max, mull) --.
Column 13, line 2, "($\nu$max, mull)" should read -- ($\gamma$max, mull) --.
Column 13, line 44, "acetonitile" should read -- acetonitrile --.

Signed and Sealed this

Twenty-third  Day of  September 1986

[SEAL]

Attest:

DONALD J. QUIGG

Attesting Officer

Commissioner of Patents and Trademarks